(12) United States Patent
Yang et al.

(10) Patent No.: US 12,270,059 B2
(45) Date of Patent: Apr. 8, 2025

(54) TEA PLANT CSFAAH6 GENE AND USE THEREOF

(71) Applicant: Anhui Agricultural University, Hefei (CN)

(72) Inventors: Tianyuan Yang, Hefei (CN); Xiaojuan Fan, Hefei (CN); Zhaoliang Zhang, Hefei (CN); Xiaocao Luo, Hefei (CN); Yunxia Xie, Hefei (CN); Xiaohong Lian, Hefei (CN); Junjie Wang, Hefei (CN); Xinpeng Zhao, Hefei (CN)

(73) Assignee: Anhui Agricultural University, Hefei (CN)

( * ) Notice: Subject to any disclaimer, the term of this patent is extended or adjusted under 35 U.S.C. 154(b) by 47 days.

(21) Appl. No.: 18/309,482

(22) Filed: Apr. 28, 2023

(65) Prior Publication Data

US 2023/0348885 A1    Nov. 2, 2023

(30) Foreign Application Priority Data

Apr. 29, 2022   (CN) .......................... 202210474208.1

(51) Int. Cl.
| | |
|---|---|
| *A01H 1/00* | (2006.01) |
| *A01H 5/12* | (2018.01) |
| *C12N 9/80* | (2006.01) |
| *C12N 15/82* | (2006.01) |

(52) U.S. Cl.
CPC ................ *C12N 9/80* (2013.01); *A01H 1/00* (2013.01); *A01H 5/12* (2013.01); *C12N 15/8251* (2013.01); *C12Y 305/01099* (2013.01)

(58) Field of Classification Search
None
See application file for complete search history.

(56) References Cited

PUBLICATIONS

Shi et al. Deep sequencing of the Camellia sinensis transcriptome revealed candidate genes for major metabolic pathways of tea-specific compounds. BMC Genomics. Feb. 28, 2011; 12:131. doi: 10.1186/1471-2164-12-131. PMID: 21356090; PMCID: PMC3056800. (Year: 2011).*

Lazar et al. Transforming growth factor alpha: mutation of aspartic acid 47 and leucine 48 results in different biological activities. Mol Cell Biol. Mar. 1988;8(3):1247-52. doi: 10.1128/mcb.8.3.1247-1252. 1988. PMID: 3285178; PMCID: PMC363269. (Year: 1988).*

Martindale et al. Length of huntingtin and its polyglutamine tract influences localization and frequency of intracellular aggregates. Nat Genet. Feb. 1998;18(2):150-4. doi: 10.1038/ng0298-150. PMID: 9462744. (Year: 1998).*

Satishkumar et al. New-Generation Vectors for Plant Transgenics: Methods and Applications. Advances in Plant Transgenics: Methods and Applications. Springer, Singapore. Nov. 16, 2019; 1st ed; 101-125; https://doi.org/10.1007/978-981-13-9624-3_5 (Year: 2019).*

Nonaka et al. Truncation and pathogenic mutations facilitate the formation of intracellular aggregates of TDP-43. Hum Mol Genet. Sep. 15, 2009;18(18):3353-64. doi: 10.1093/hmg/ddp275. Epub Jun. 10, 2009. PMID: 19515851. (Year: 2009).*

* cited by examiner

*Primary Examiner* — Phuong T Bui
*Assistant Examiner* — Dequantarius Javon Speed
(74) *Attorney, Agent, or Firm* — Venable LLP; Keith G. Haddaway; Qian Huang

(57) ABSTRACT

The present disclosure provides a tea plant CsFAAH6 gene and use thereof. The tea plant CsFAAH6 gene has a nucleotide sequence shown in SEQ ID NO: 1 in sequence listing. A protein coded by the tea plant CsFAAH6 gene has an amino acid sequence shown in SEQ ID NO: 2 in the sequence listing. The CsFAAH6 is highly expressed in mature leaves of tea plants; there is significant negative correlation between theanine content in shoots (one bud and two leaves) of different tea cultivars in different months and expression level of the CsFAAH6; instantaneous silencing of CsFAAH6 expression can significantly increase the theanine content, indicating that CsFAAH6 has a physiological function of theanine degradation and a molecular mechanism thereof.

2 Claims, 19 Drawing Sheets

Specification includes a Sequence Listing.

TEA PLANT CSFAAH6 GENE AND USE THEREOF

CROSS REFERENCE TO RELATED APPLICATION

This patent application claims the benefit and priority of Chinese Patent Application No. 202210474208.1, filed with the China National Intellectual Property Administration on Apr. 29, 2022, the disclosure of which is incorporated by reference herein in its entirety as part of the present application.

REFERENCE TO SEQUENCE LISTING

The instant application contains a Sequence Listing which has been submitted electronically in XML format and is hereby incorporated by reference in its entirety. The name of the text file containing the sequence listing is HLP20230301381-Sequence listing.xml, has a file size of 16,167 bytes, and was created on Apr. 27, 2023.

TECHNICAL FIELD

The present disclosure relates to the technical field of genetic engineering, in particular to a tea plant CsFAAH6 gene and use thereof.

BACKGROUND

China is the world's largest tea producing and consuming country. In 2020, according to data from the China Tea Marketing Association, the current tea planting area and output in China reached 3.165 million hectares and 2.986 million tons, respectively. Theanine is the main flavor substance that confers fresh taste and health benefits on green tea. The accumulation of theanine in tea shoots is co-regulated by the environment and genetics. The theanine content is dynamically regulated by factors such as root synthesis and storage, long-distance transport from roots to tea shoots, and accumulation and degradation in shoots. Studying the function and mechanism of CsFAAH6-mediated intracellular metabolism of theanine in tea plants to regulate theanine accumulation will help understand the molecular mechanism of dynamic regulation of intracellular theanine metabolism and accumulation in tea shoots. The theanine content in tea shoots is increased by regulating the expression of CsFAAH6, providing genetic resources and theoretical support for improving tea quality and tea farmers' economic benefits.

SUMMARY

An objective of the present disclosure is to provide a tea plant CsFAAH6 gene and use thereof. Transient silencing of CsFAAH6 can significantly increase theanine in tea shoots, and provide theoretical support and functional gene resources for breeding new tea cultivars with high theanine by molecular assisted breeding.

The present disclosure is accomplished based on the following findings of the inventors: there is significant negative correlation between expression level of the CsFAAH6 gene encoded by fatty acid amide hydrolase (FAAH) and theanine content in tea shoots and roots. The inventors have analyzed the correlation between expression levels of six genes (CsFAAH1/2/3/4/5/6) of the tea plant CsFAAHs family with the theanine content and finally determined that the CsFAAH6 gene is an important candidate gene encoded by theanine hydrolase.

In a first aspect of the present disclosure, a tea plant CsFAAH6 gene is provided, where the tea plant CsFAAH6 gene has a nucleotide sequence shown in SEQ ID NO: 1 in sequence listing.

Further, the present disclosure further provides a protein sequence encoded by the tea plant CsFAAH6 gene, where a protein sequence is shown in SEQ ID NO: 2 in the sequence listing.

In another aspect of the present disclosure, a tea plant expression vector pCAMBIA1305.1-CsFAAH6 is provided, where the expression vector is obtained by digesting a fragment shown in SEQ ID NO: 1 into a vector pCAMBIA1305.1.

In another aspect of the present disclosure, use of a tea plant CsFAAH6 gene in altering theanine content in tea shoots and roots is provided.

In another aspect of the present disclosure, a method is provided for using a tea plant CsFAAH6 gene to alter theanine content in tea shoots and roots, including the following steps:
  cloning the tea plant CsFAAH6 gene;
  constructing a tea plant expression vector; and
  transforming the tea plant expression vector into the tea shoots and roots.

Further, the tea plant expression vector is pCAMBIA1305.1-CsFAAH6.

Further, after the tea plant expression vector is transformed into the tea shoots and roots, transiently silencing the expression of CsFAAH6 in the shoots and roots by antisense oligonucleotides increases the theanine content in the tea shoots and roots.

Compared with the prior art, the present disclosure has the following beneficial effects:

The present disclosure puts forward a hypothesis on the basis of previous studies, and clones the CsFAAH6 gene. Through the antisense oligonucleotide silencing experiment, it is found that there is significant negative correlation between expression level of the CsFAAH6 gene and theanine in tea shoots, and inhibiting the expression of the CsFAAH6 gene can reduce the degradation of theanine in the tea plant and increase the accumulation of the theanine in the tea shoots. The present disclosure provides a recombinant plasmid containing CsFAAH6 and a transgenic engineering bacterium (a new engineering bacterium obtained by transforming a pEASY-Blunt::CsFAAH6 plasmid into an *Escherichia coli* DH5a competent cell). Meanwhile, the present disclosure enriches the theoretical content of the intracellular metabolism regulation of the theanine in the tea plant, and further provides a target gene for improving the tea shoot theanine content and tea quality.

DETAILED DESCRIPTION OF THE EMBODIMENTS

Figure 1A:
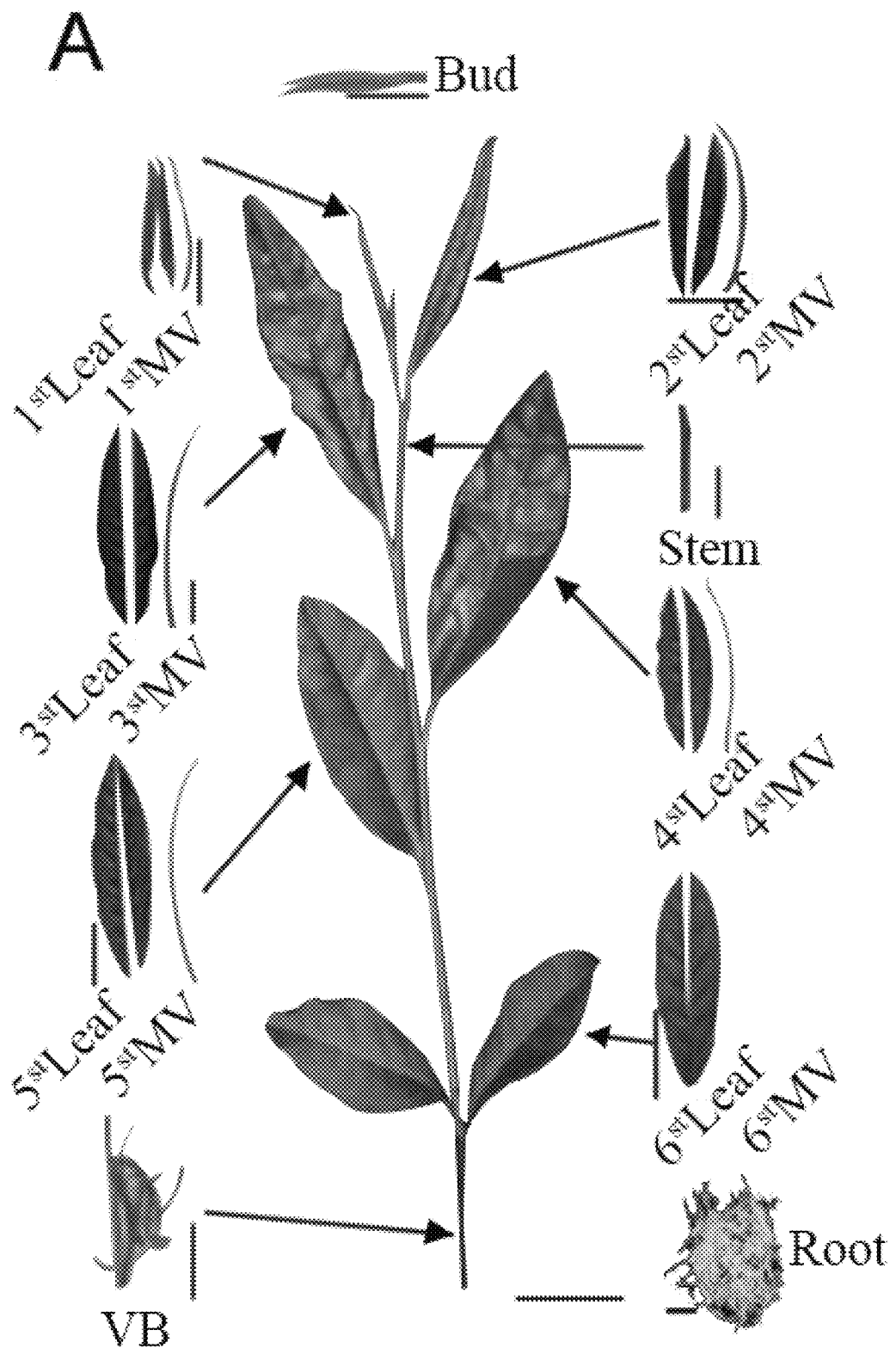
FIG. 1A illustrates phenotypes of different tissues and organs of a tea plant.

Technical solutions in the example of the present disclosure will be clearly and completely described below with reference to the accompanying drawings in the example of the present disclosure. Apparently, the described example is only a part of, but not all of, the examples of the present disclosure. Based on the example of the present disclosure, all other examples obtained by those of ordinary skill in the art without creative efforts shall fall within the protection scope of the present disclosure.

1. Cloning and Sequence Structure Analysis of the CsFAAH6 Gene

The tea plant CsFAAH6 gene is a tea plant fatty acid amide hydrolase encoding gene, and cloning and sequence structure analysis thereof are specifically as follows:

The cultivar *C. sinensis* cv. Shuchazao was planted in the Nongcuiyuan, Anhui Agricultural University, Anhui Province, and young roots were used for RNA extraction. Total RNA was extracted using RNAprep Pure Plant Kit (Tiangen, Beijing, China) in accordance with the instructions. The RNA content and quality were detected by using a spectrophotometer.

The first strand was generated by reverse transcription: with 1 µg of RNA as a template, a reaction buffer was prepared according to the instructions of PrimeScript II 1st Strand cDNA Synthesis Kit (Takara Biotech, China), where 0.6 µL of Oligo dT Primer (50 µM), 0.4 µL of Random 6mers (50 µM), and 1 µL of dNTP Mixture (10 mM each) were added, and the reaction system was made up to 10 µL with RNase Free ddH$_2$O; the RNA was denatured at 65° C. for 5 min and immediately placed on ice. Subsequently, the above reaction buffer was added with 4 µL of 5× PrimerScript Buffer, 0.5 µL of RNase Inhibitor (40 U), and 1 µL of PrimerScript RTase (200 U), made up to 20 µL with ddH$_2$O, and incubated at 42° C. for 45 min. and reverse transcriptase was inactivated at 95° C. for 5 min. After optimization, a quantity of reverse transcription product was taken for subsequent PCR. The CsFAAH6 gene was amplified by conventional PCR using the first-strand cDNA as an RT-PCR template. The upstream primer was 5'-ATGGGCATTTTCAAGGCCAA-3' (SEQ ID NO: 3), and the downstream primer was 5'-TCAATCCTTTTGAGCAGATCA-3' (SEQ ID NO: 4). The 20 µL PCR system was: 2.5 µL of 10×Ex Taq buffer, 2.0 µL of dNTP, 1 µL each of upstream and downstream primers, 0.2 µL of Ex Taq, 1 µL of template, and 15.8 µL of ddH$_2$O.

The reaction program was as follows: initial denaturation at 98° C. for 10 s, 35 cycles of denaturation at 98° C. for 10 s, annealing at 57° C. for 30 s, and extension at 72° C. for 2 min; and extension at 72° C. for 10 min. The PCR product CsFAAH6 gene was purified, recovered, and ligated to the pEASY-Blunt Vector (Promega, Shanghai, China) to obtain a pEASY-Blunt::CsFAAH6 plasmid, which was transformed into *E. coli* DH5a Competent Cells and sent to GM for sequencing. The nucleotide sequence of the resulting CsFAAH6 gene obtained is shown in SEQ ID NO: 1 in the sequence listing, which was specifically shown as follows:

ATGGGCATTTTCAAGGCCAAAGGCGTAGTCTACAAGCCTGTCGACGAT

GTCGATCTCGGTCCTCACAGCGATGAGTTTTATCTCCGTGCTAACGTCA

AAGCTCCTCGCATGGCTGGATTGCTGGTTAAAATTTTTGTTTGGTTCCT

CGAGTCGCGGATTTTCGGGGGTATTTTGTTGTACATGTTGAAGAGAAAC

AACCTAATTCACAAGCTTGTTTCATATGCAGAGTTGGAAGAGTCACCTG

TATTTGTTCCTTCACACCCTTATGAAGGCCTTAAAGAACAAGAAGTCAA

ATTAGTAGAGGATGATCTCTCTCCATCTGACAAAATTCAGAAGGCCATG

GAATGCATACAATGCTCAGAAAGTATACAAGAAAATTCGGAGCTTAGTT

TCCATCGCTGGACAGTATTGGATTATTCAAGAGCTTACATTTCAGGAGA

GATTACTCCTCTCATGGTGGCGGAGCGATTTATAGCTGCTGTCCATGAA

TCGTCTGAACCTGCATTGCACATGTCATTCTTTATTGATTATAATGTTG

GAGACATATTAAGGCAAGCTACTGAGTCAACTCAGCGGTACAAACAAGG

AGAACCATTATCACCTCTAGATGGAGTCCCAATCGCAATCAAAGACGAA

ATAGATTGTATGCCCTATCCAACTACAGGGGGTACAAAGTGGTTGCAAA

AGGTAAGACATTGTGCAGATGATGCATGCTGTGTTAAGCGCCTGAGATT

ATGTGGTGCCATACTTGTTGGGAAGACAAATATGCATGAGCTCGGGGCT

GGAACCAGTGGTATCAATCCTCATTATGGGGTACCTAGAAATCCATATG

ATCCCAACAAGGTCTCTGGGGGTTCTTCTAGTGGATCTGCAGCTGTGGT

TTCTGCAGGGTTGTGCCCTGTTGCCCTAGGTGTTGATGGGGGAGGATCT

GTGAGAATGCCTGCTGCTCTTTGTGGTGTTGTTGGTCTGAAGCCAACTT

TTGGACGTGTGCCCCATTCTGGTGTTATTCCTCTGAACTGGACAGTTGG

GATGGTCGGTATCCTAGCAGGCACAGTTGAAGATGCATTTATTACTTAT

GCAGCTATCAGTGGTCAATTTCCATCATGCCAACCCACAGATGCAGTGA

AAAAAATTAATTTCCCACTCCTGAAGACACCAAACTGTATATCTAACAT

CAAGATGGCTAAATATGGGGAGTGGTTTAATGATTGCACCGACGACATC

AGAGTCTGTTGTTCCCATGCTCTGGACCAGCTTCACAAGCATTATGGAT

GGGAGACCATGGACGTGACCATACCAGAGATAGAGGTGATGCGCCTGGC

GCATTATTCAACAATTGGATCGGAGTGTAGCAATTCAATTGCTTGTCAT

CTTGAAAACATGAATGTGGCAGAAATAGGGTTGGATGCAAGAGTAGCAC

TCTCTGTTTATGGTTCTTTCAGCAGCAGGGAGTATTTGAATGCCCAGAA

AATTAGGAACCGACAGATGCAGTTTCATAAGAAAATATTTGCCATGGCA

-continued

```
GATGTTATTGTTACACCAACGACAGGTGTGACTGCCTACCCAATATTCG

ATGATGCTTTGAAAACTGGGGAACTTGACTACATAAATGGAGCTGCACT

TGTTCGGTATCAGATATCAGGAAATTTCTTGGGATTGCCAGCAGTAACC

ATACCTATTGGATACGACAAAGTTGGCTTGCCTATAGGCCTTCAATTTA

TTGGGAAGCCATGGTCCGAAGCTACGCTGATCCACATAGCGTTCGCAAT

GCAGGCCATCTCGGACTCAAAAAAACCACAGATTTTCTATGATCTGCTC

AAAAAGGATTGA
```

The protein sequence encoded by the CsFAAH6 gene was specifically shown in SEQ ID NO: 2 in the sequence listing:

```
MGIFKAKGVVYKPVDDVDLGPHSDEFYLRANVKAPRMAGLLVKIFVWF

LESRIFGGILLYMLKRNNLIHKLVSYAELEESPVFVPSHPYEGLKEQEV

KLVEDDLSPSDKIQKAMECIQCSESIQENSELSFHRWTVLDYSRAYISG

EITPLMVAERFIAAVHESSEPALHMSFFIDYNVGDILRQATESTQRYKQ

GEPLSPLDGVPIAIKDEIDCMPYPTTGGTKWLQKVRHCADDACCVKRLR

LCGAILVGKTNMHELGAGTSGINPHYGVPRNPYDPNKVSGGSSSGSAAV

VSAGLCPVALGVDGGGSVRMPAALCGVVGLKPTFGRVPHSGVIPLNWTV

GMVGILAGTVEDAFITYAAISGQFPSCQPTDAVKKINFPLLKTPNCISN

IKMAKYGEWFNDCTDDIRVCCSHALDQLHKHYGWETMDVTIPEIEVMRL

AHYSTIGSECSNSIACHLENMNVAEIGLDARVALSVYGSFSSREYLNAQ

KIRNRQMQFHKKIFAMADVIVTPTTGVTAYPIFDDALKTGELDYINGAA

LVRYQISGNFLGLPAVTIPIGYDKVGLPIGLQFIGKPWSEATLIHIAFA

MQAISDSKKPQIFYDLLKKD
```

2. Analysis of Differential Expression of CsFAAH6 Gene (1) Expression of CsFAAH6 Gene in Different Tissues of Tea Plant The national elite tea cultivar *C. sinensis* cv. Shuchazao was planted in Nongcuiyuan. Anhui Agricultural University, Luyang District, Hefei, Anhui Province, and 16 tissues and organs were used to analyze gene expression. The 16 tissues and organs included bud, $1^{st}$ leaf, $1^{st}$ main vein, $2^{nd}$ leaf, $2^{nd}$ main vein, $3^{rd}$ leaf, $3^{rd}$ main vein, $4^{th}$ leaf, $4^{th}$ main vein, $5^{th}$ leaf, $5^{th}$ main vein, $6^{th}$ leaf, $6^{th}$ main vein, vascular bundle, shoot between $2^{nd}$ and $3^{rd}$ leaves (stem), and roots. Also, these samples were used for total RNA extraction and first-strand cDNA synthesis. The reverse transcription product (first-strand cDNA) was diluted 5-fold as a template, and a 10 μL reaction system was prepared using 2×AceQ Universal qPCR SYBR9@ Master Mix (Vazyme, Nanjing, China): 1.0 μL of 5-fold diluted reverse transcription product, 0.4 μL each of upstream and downstream primers (10 μmol/μL), 5 μL of 2×AceQ Universal qPCR SYBR® Master Mix, and 3.2 μL of ddH$_2$O. Three replicates were prepared for each reaction. Subsequently, the following program was run on the Bio-rad CFX-384 Touch System: i) initial denaturation at 95° C. for 5 min; ii) 40 cycles of denaturation at 95° C. for 10 s, annealing at 60° C. for 30 s, and extension at 72° C. for 30 s; and iii) from 65° C. to 95° C., to plot the melting curve at 0.1° C./s. The upstream primer was 5'-GTTCTITCAGCAGCAGGGAG-3' (SEQ ID NO: 5), and the downstream primer was 5'-CGAACAAGTGCAGCTC-CATT-3' (SEQ ID NO: 6). With tea plant CsGADPH gene as internal reference, based on the upstream primer (5'-TTGG-CATCGTTGAGGGTCT-3') (SEQ ID NO: 7) and the downstream primer (5'-CAGTGGGAACACGGAAAGC-3') (SEQ ID NO: 8), the relative expression levels of CsFAAH6 in different tissues were calculated through the analysis software of the instrument.

Figure 1B:
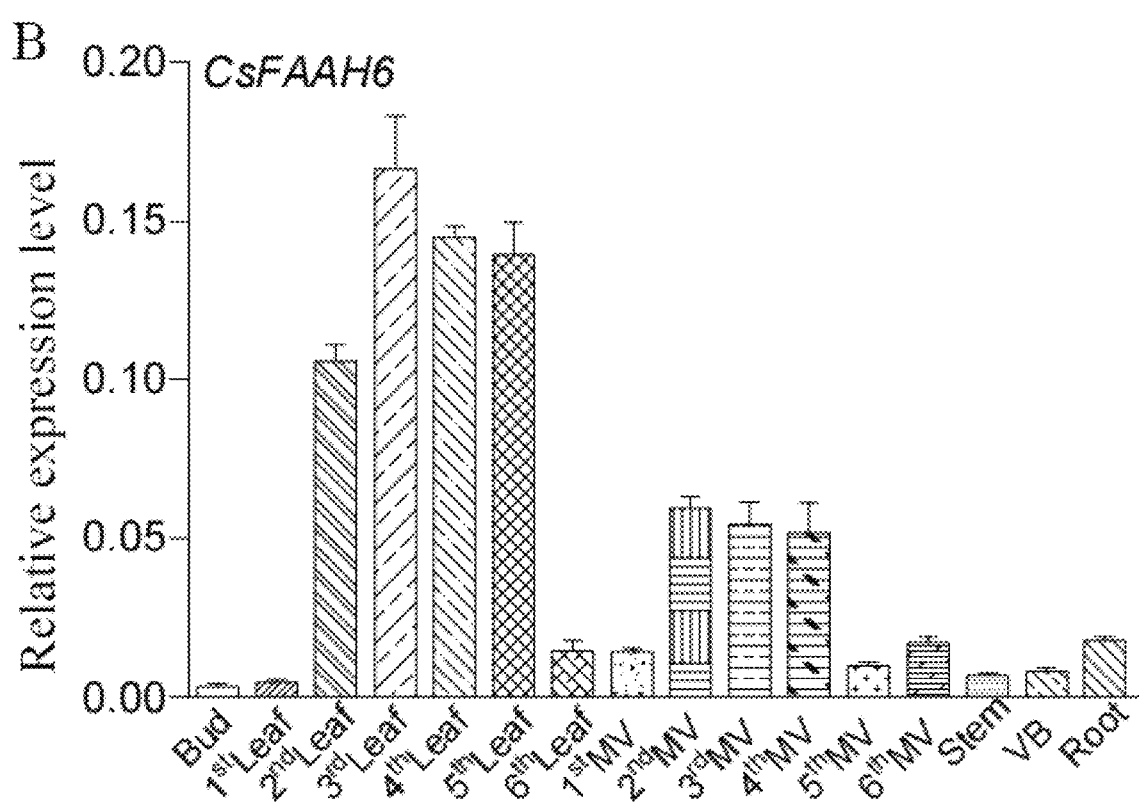
FIG. 1B illustrates expression patterns of tea plant CsFAAH6 in different tissues of a tea plant.
Figure 2A:
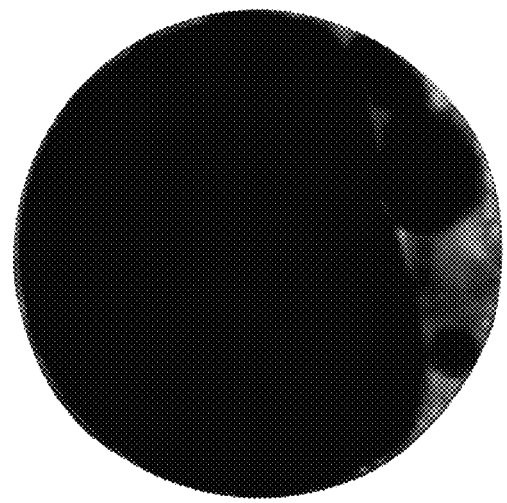
FIGS. 2A-F illustrates subcellular localization of tea plant CsFAAH6.
Figure 2B:
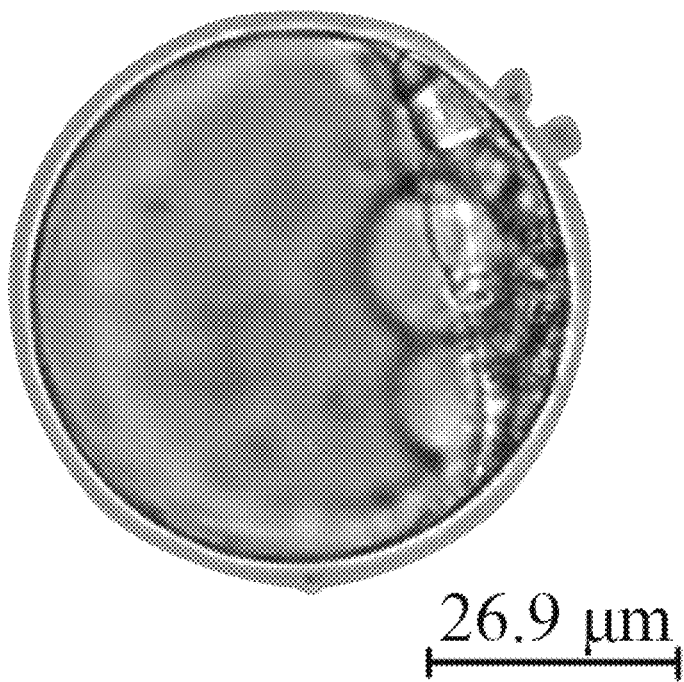
Figure 2C:
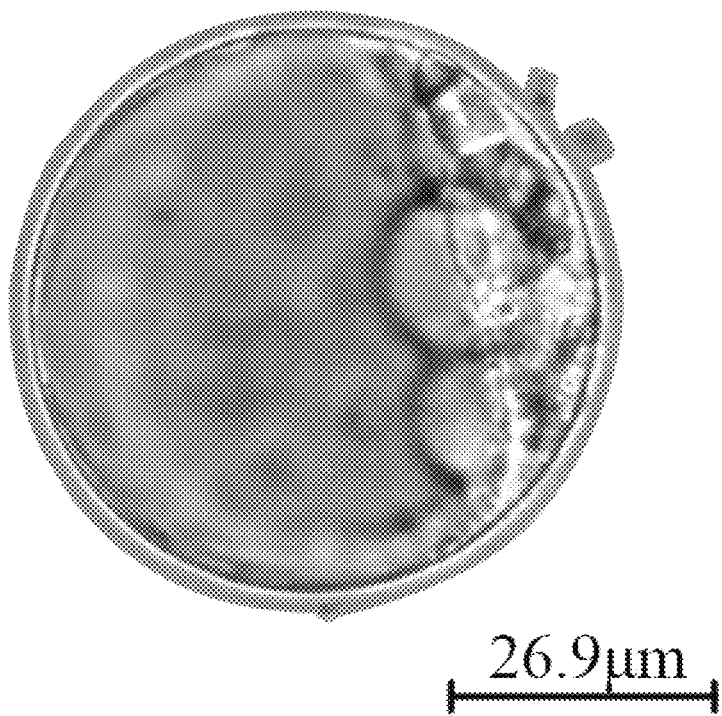
Figure 2D:
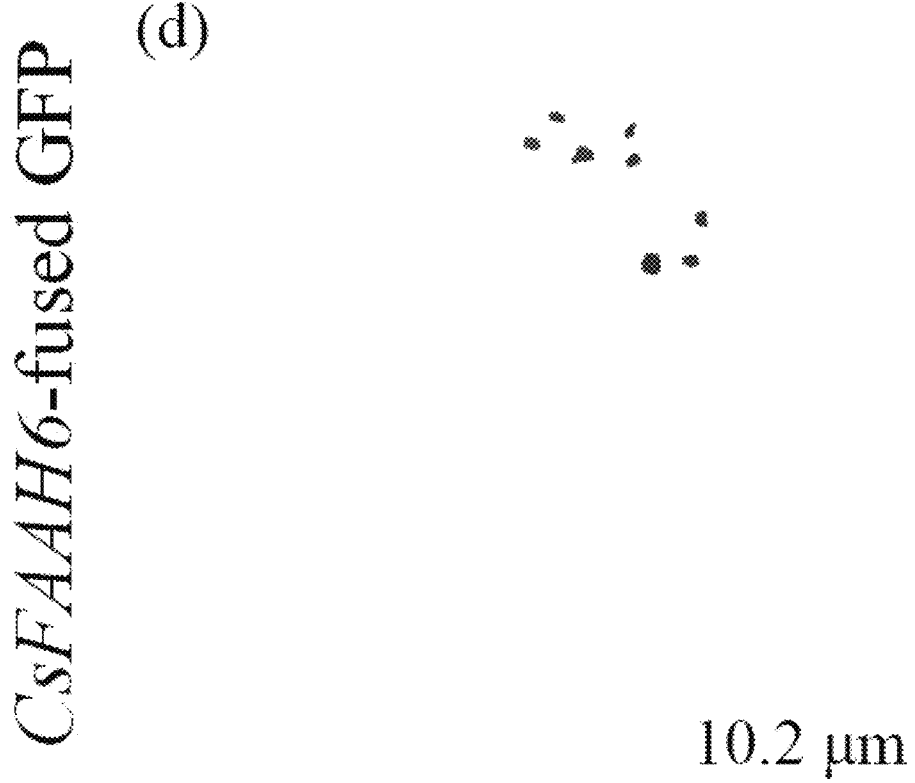
Figure 2E:
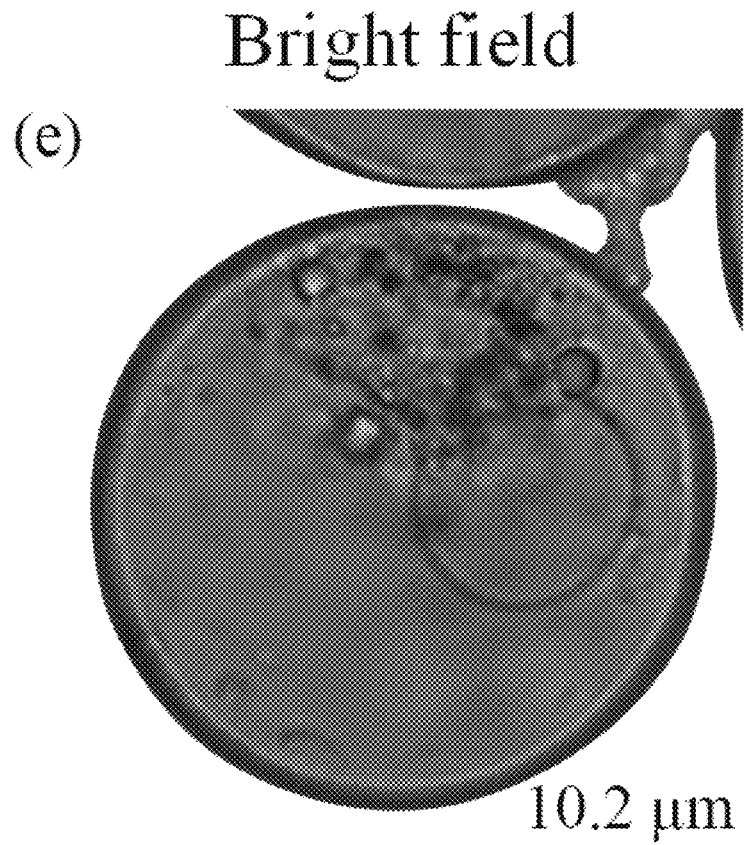
Figure 2F:
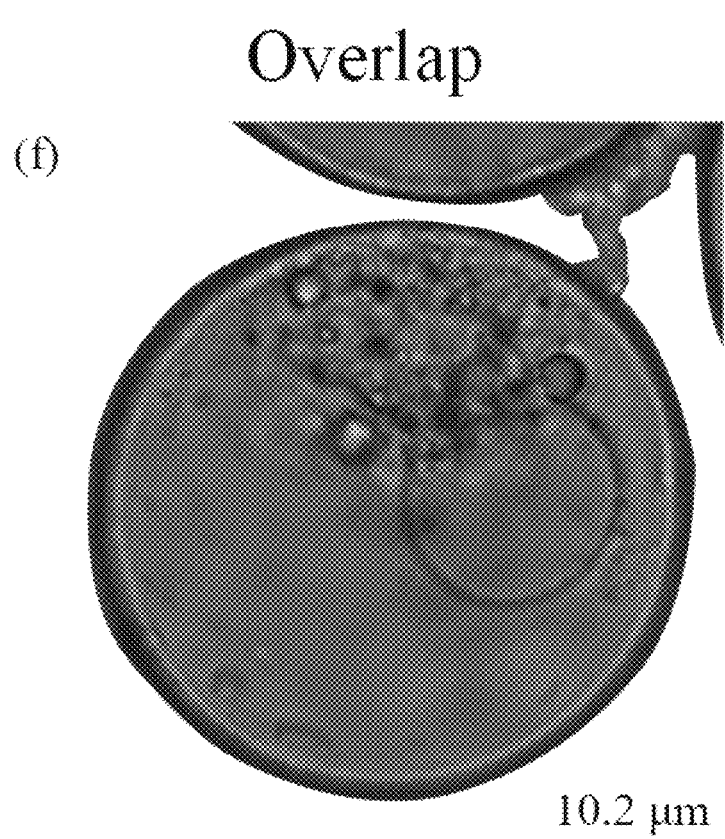
Figure 3A:
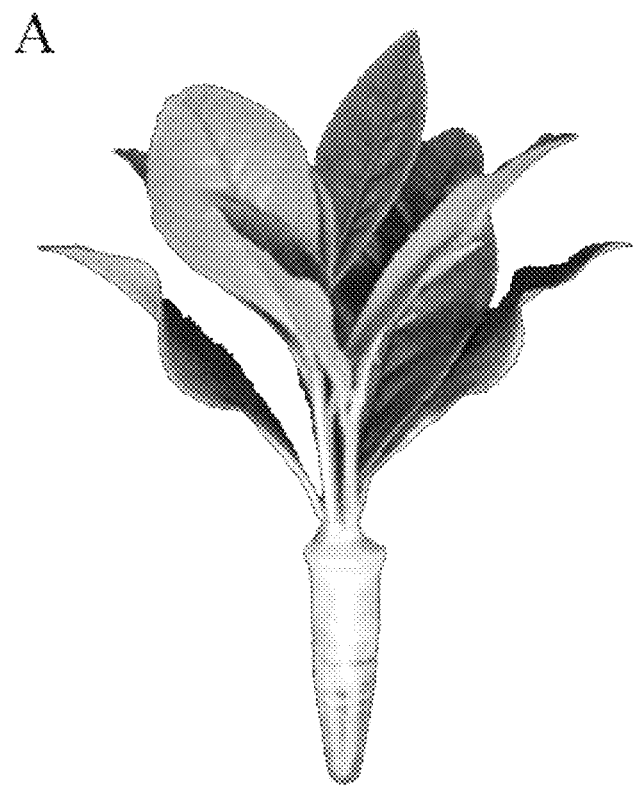
FIG. 3A and FIG. 3B illustrate a process of a transient silencing test of CsFAAH6 gene in tea shoots.
Figure 3B:
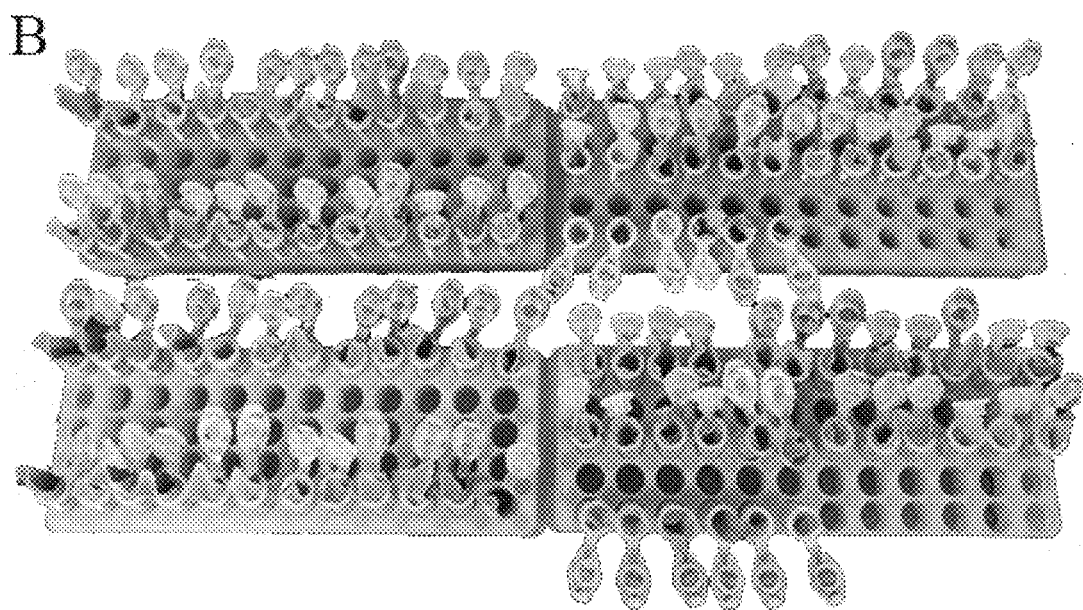
Figure 3C:
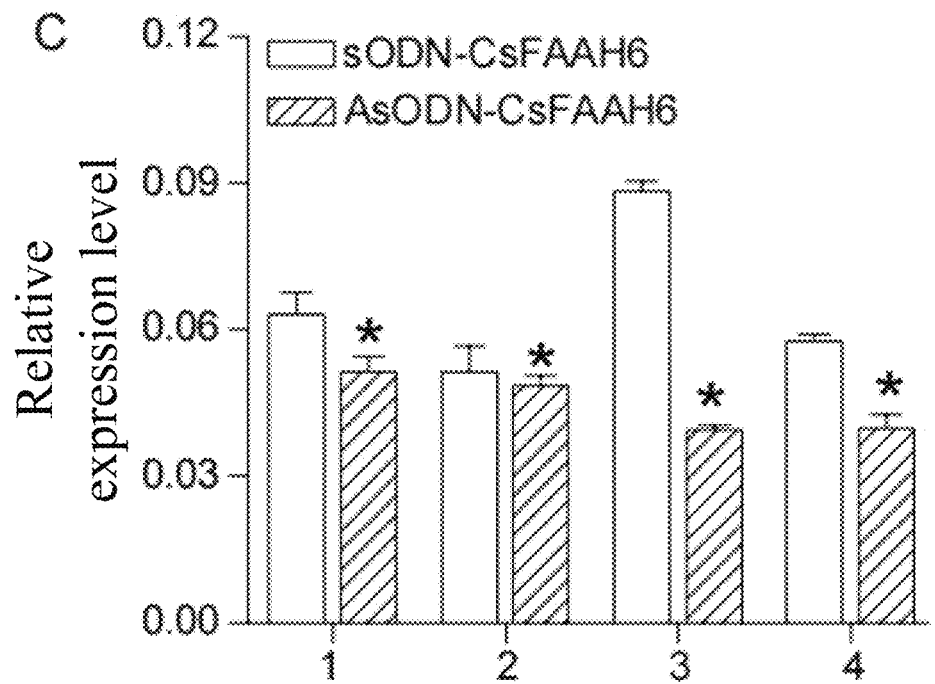
FIG. 3C illustrates the detection of CsFAAH6 gene expression after the silencing test.
Figure 3D:
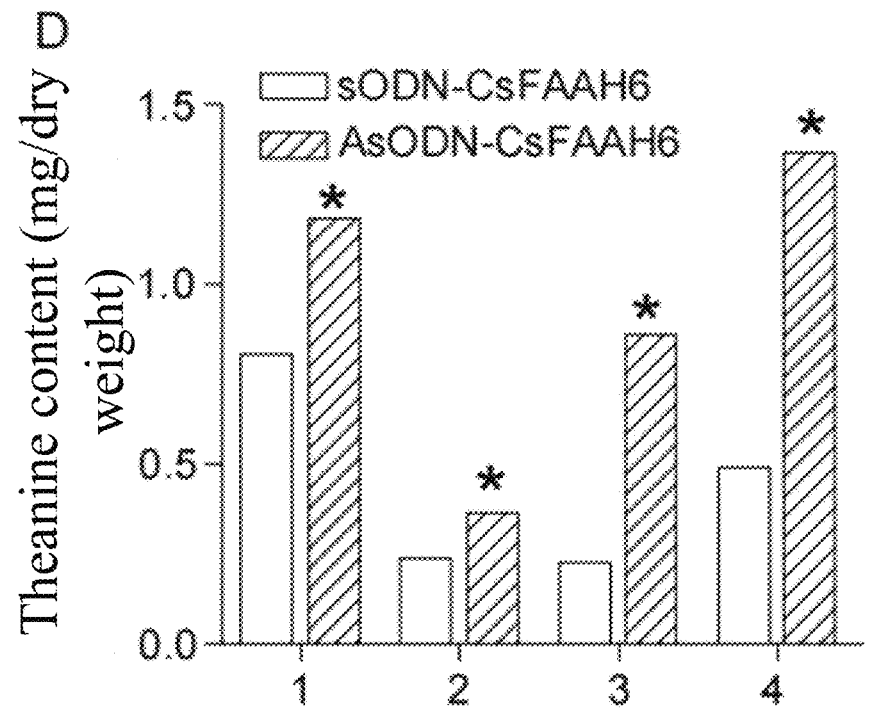
FIG. 3D illustrates the theanine content in the CsFAAH6 gene silenced tea shoots.
Figure 4A:
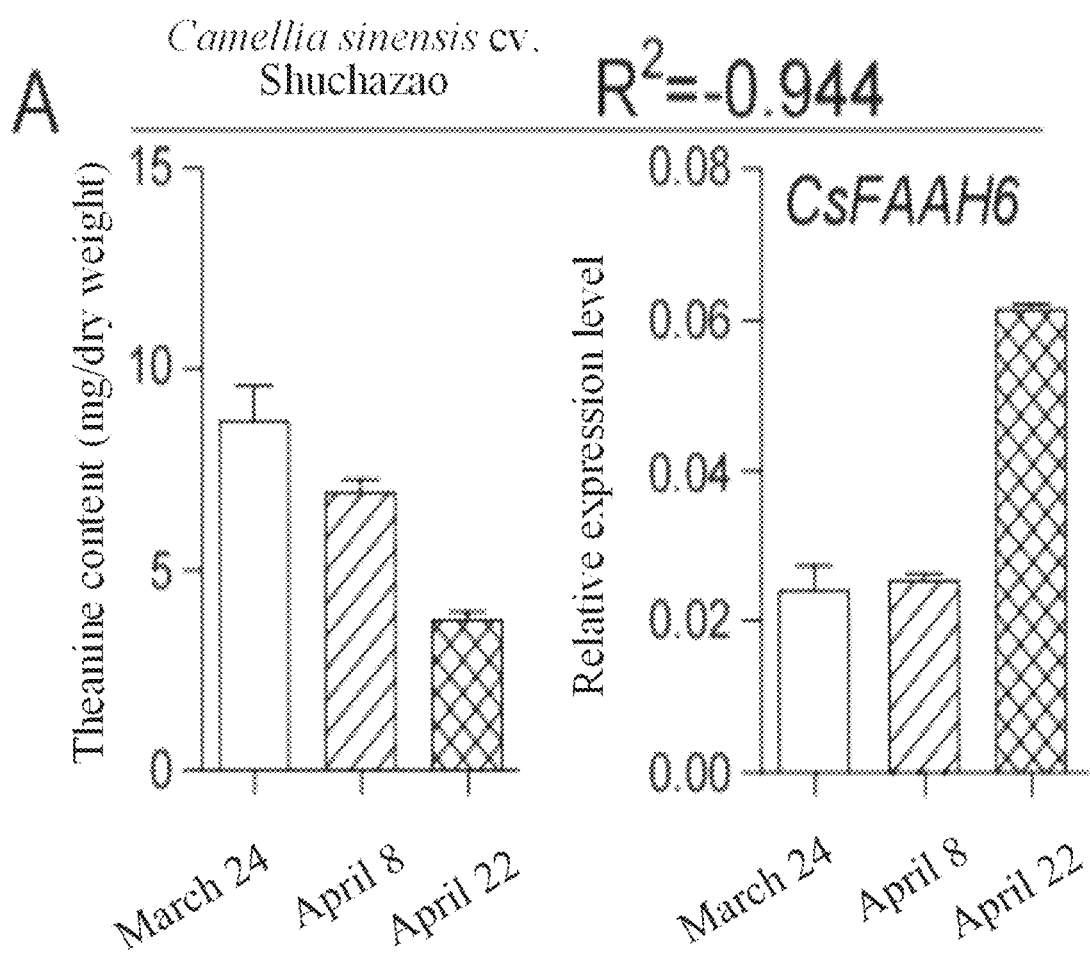
FIG. 4A illustrates the correlation between expression levels of CsFAAH6 in *Camellia sinensis* cv. Shuchazao and theanine content in tea shoots.
Figure 4B:
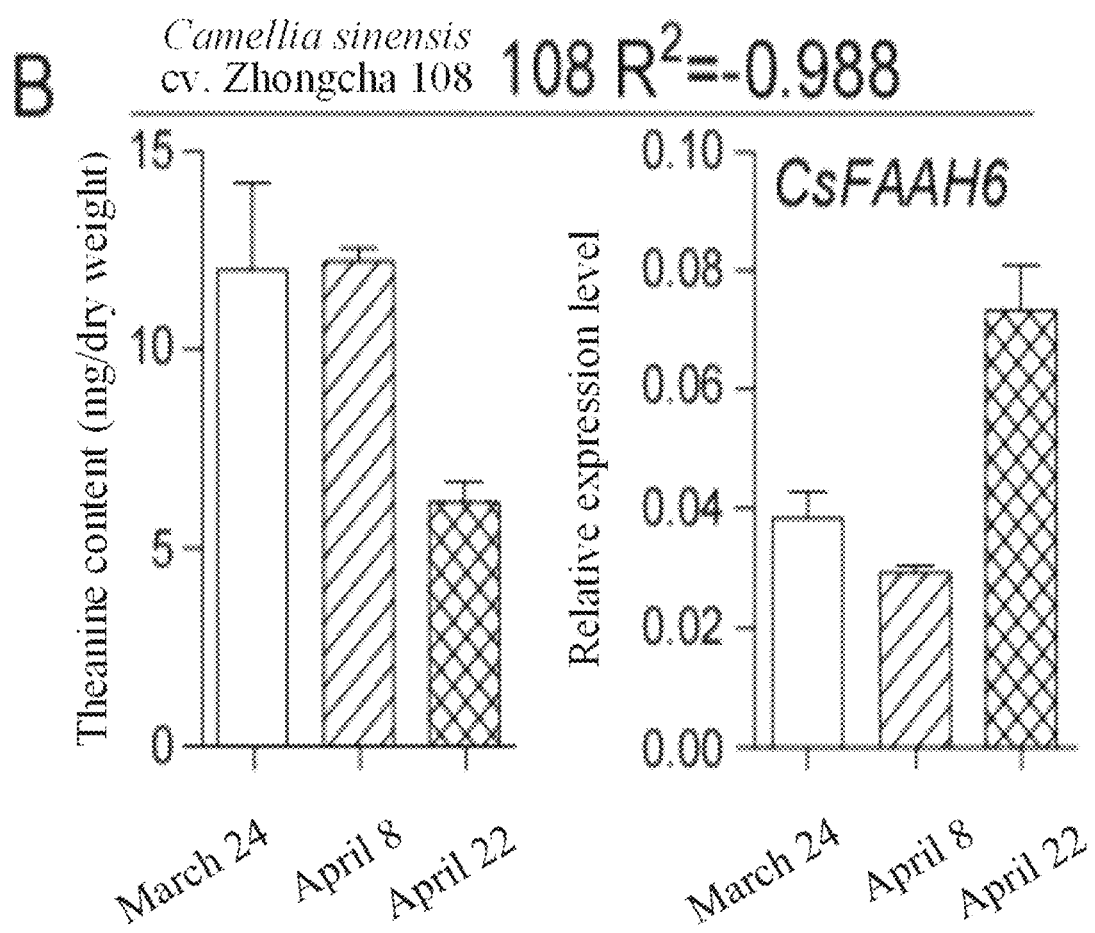
FIG. 4B illustrates the correlation between expression levels of CsFAAH6 in *C. sinensis* cv. Zhongcha 108 and theanine content in tea shoots.
Figure 4C:
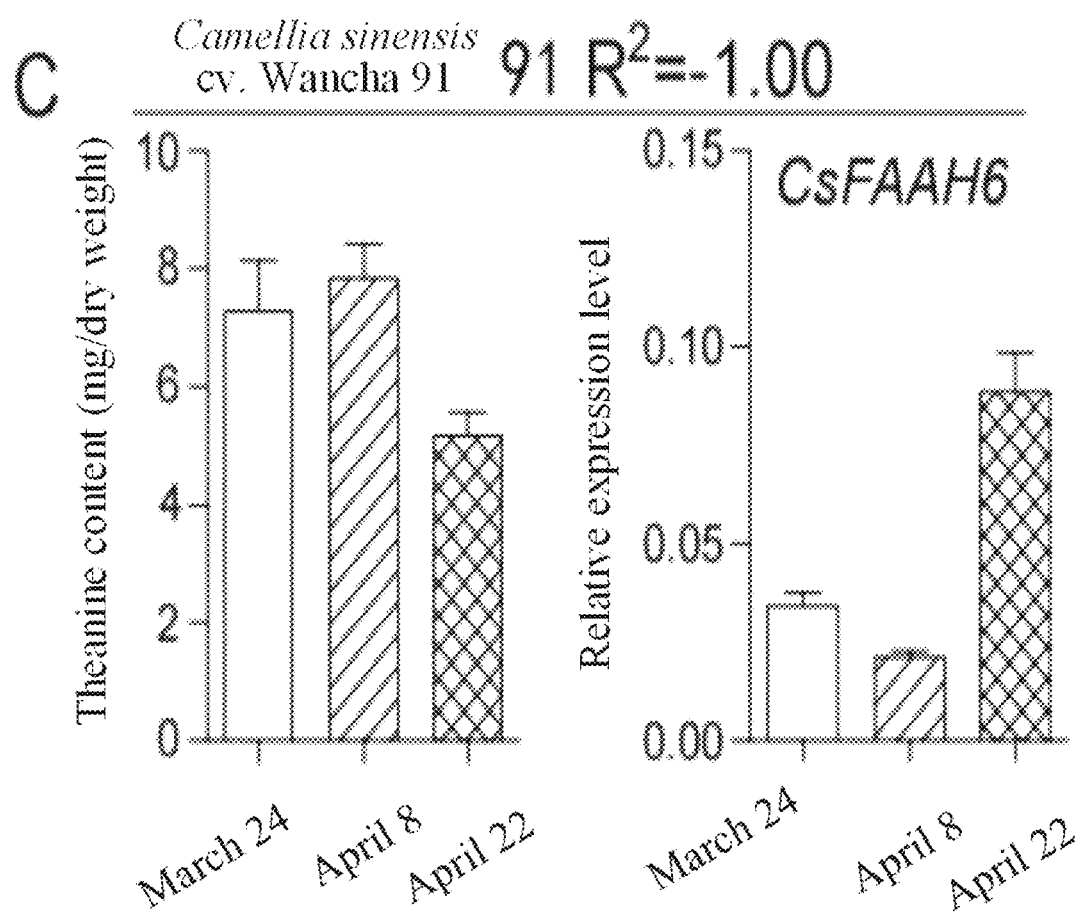
FIG. 4C illustrates the correlation between expression levels of CsFAAH6 in *C. sinensis* cv. Wancha 91 and theanine content in tea shoots.
Figure 4D:
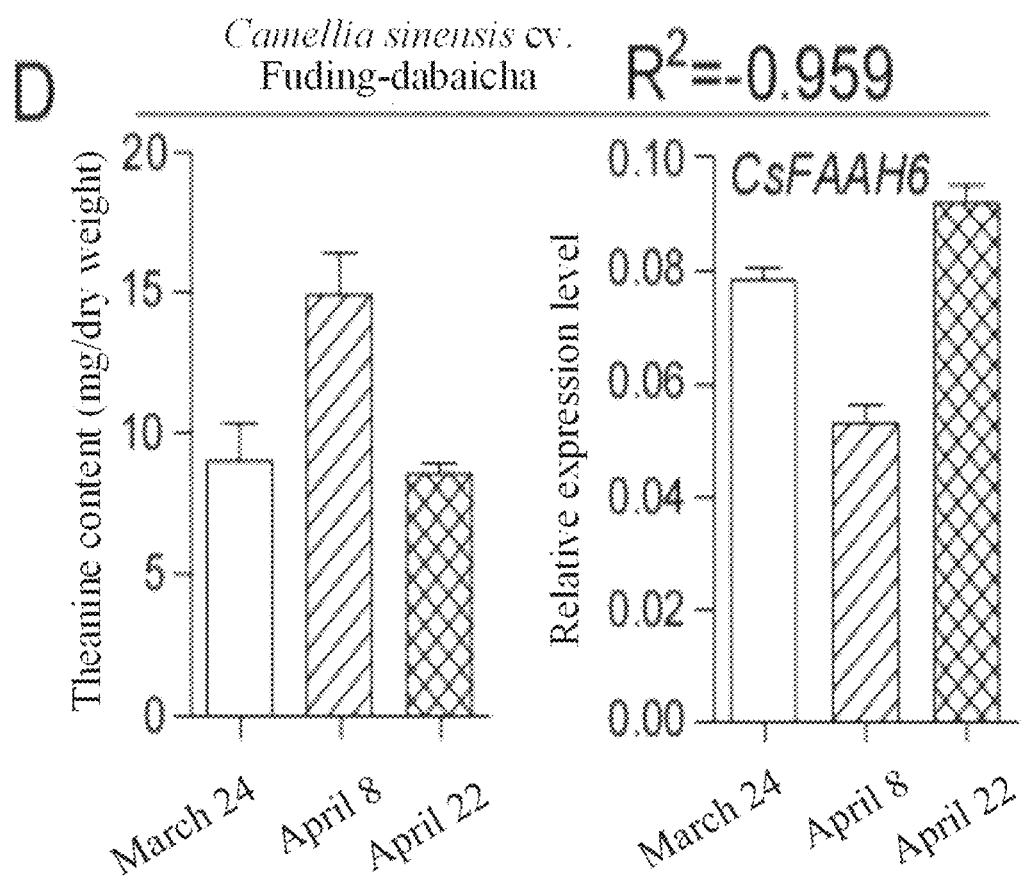
FIG. 4D illustrates the correlation between expression levels of CsFAAH6 in *C. sinensis* cv. Fuding-dabaicha and theanine content in tea shoots.
Figure 4E:
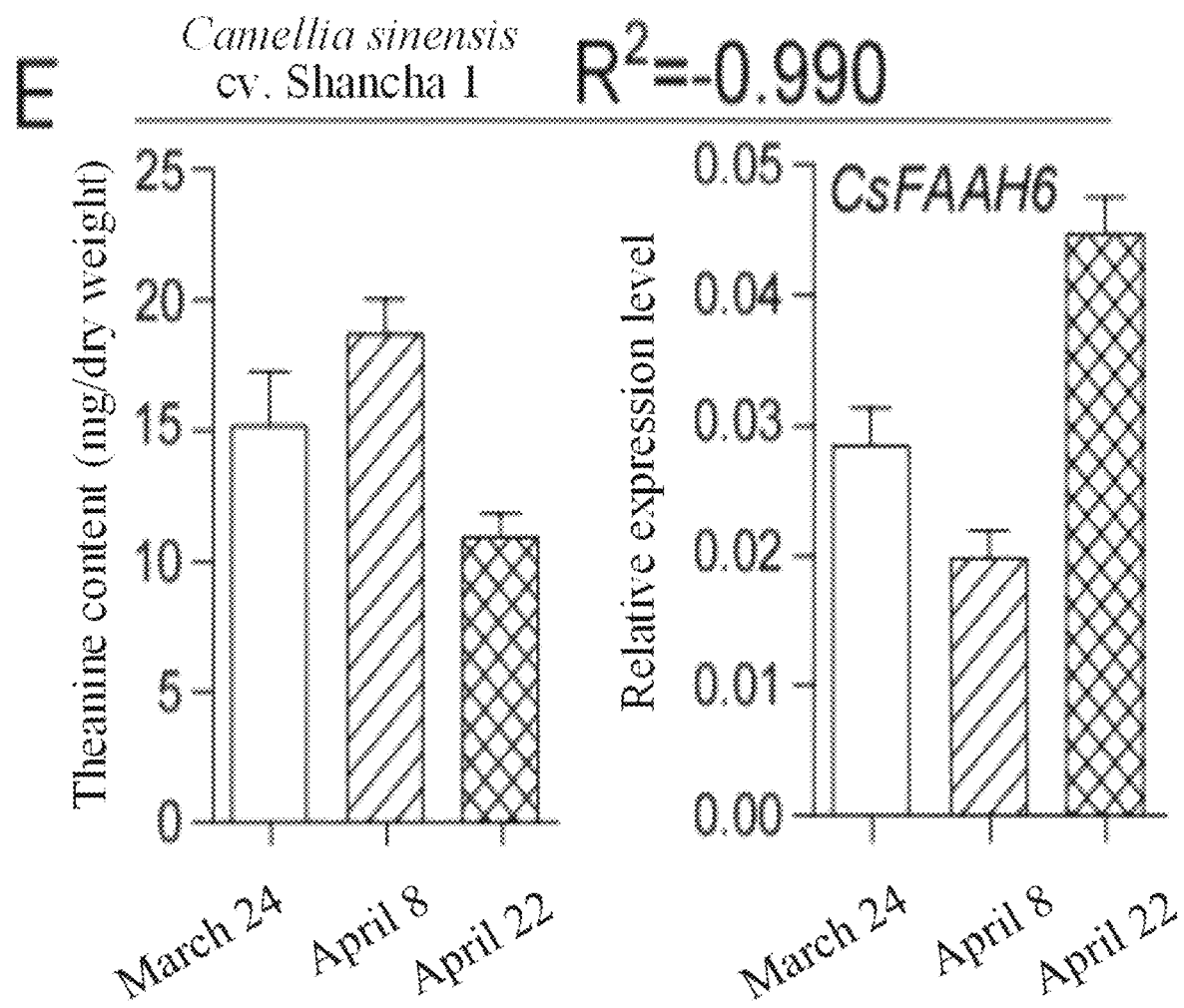
FIG. 4E illustrates the correlation between expression levels of CsFAAH6 in *C. sinensis* cv. Shancha 1 and theanine content in tea shoots.
Figure 4F:
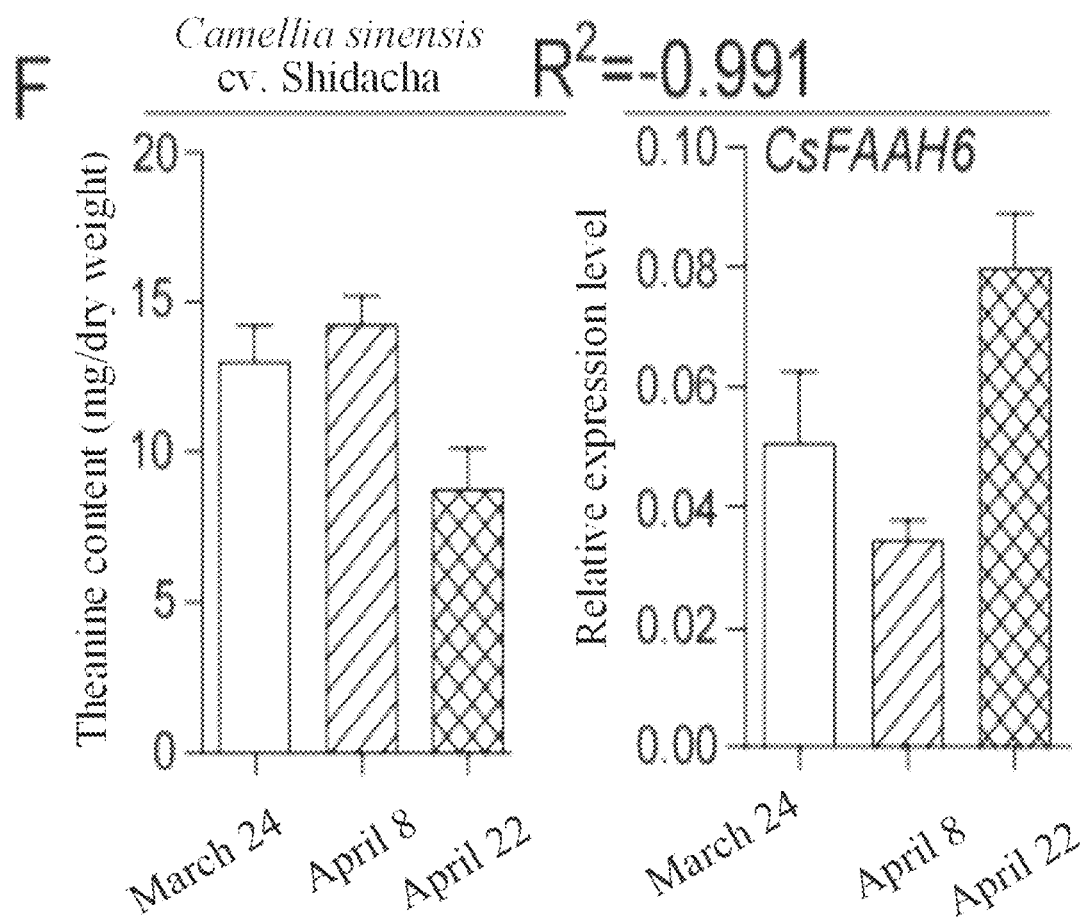
FIG. 4F illustrates the correlation between expression levels of CsFAAH6 in *C. sinensis* cv. Shidacha and theanine content in tea shoots.
Figure 4G:
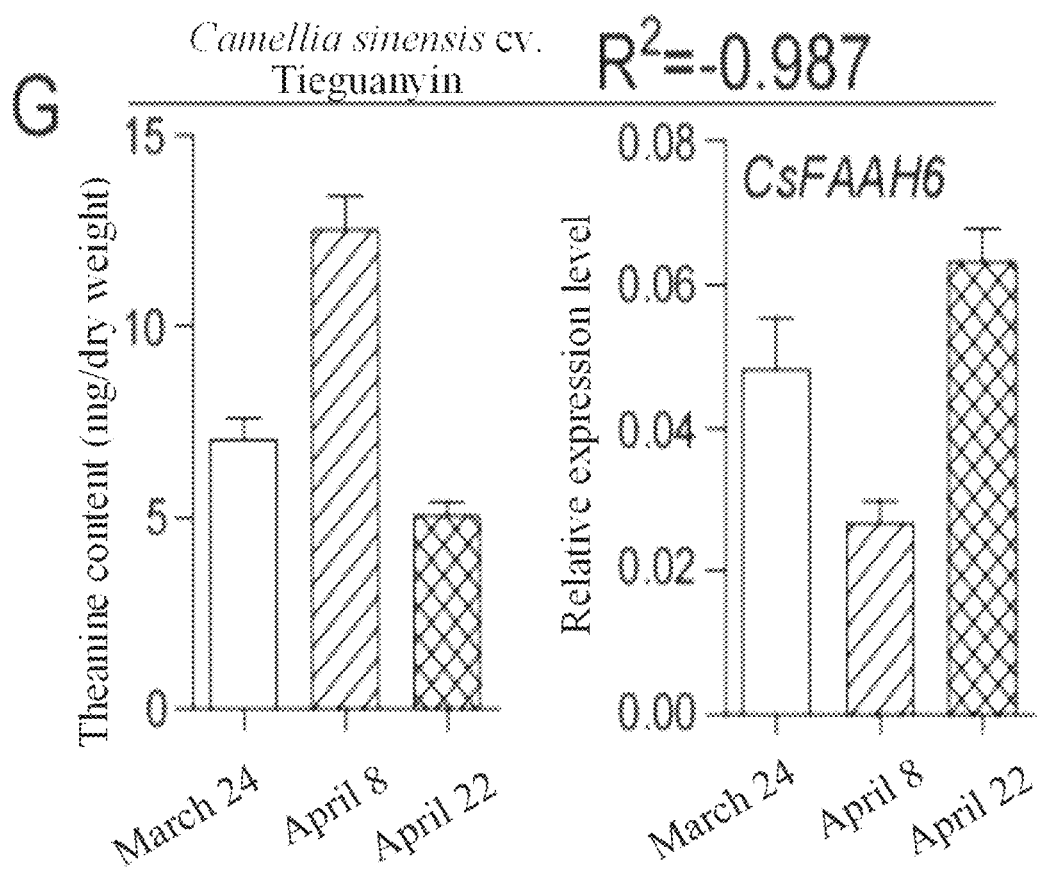
FIG. 4G illustrates the correlation between expression levels of CsFAAH6 in *C. sinensis* cv. Tieguanyin and theanine content in tea shoots.
Figure 4H:
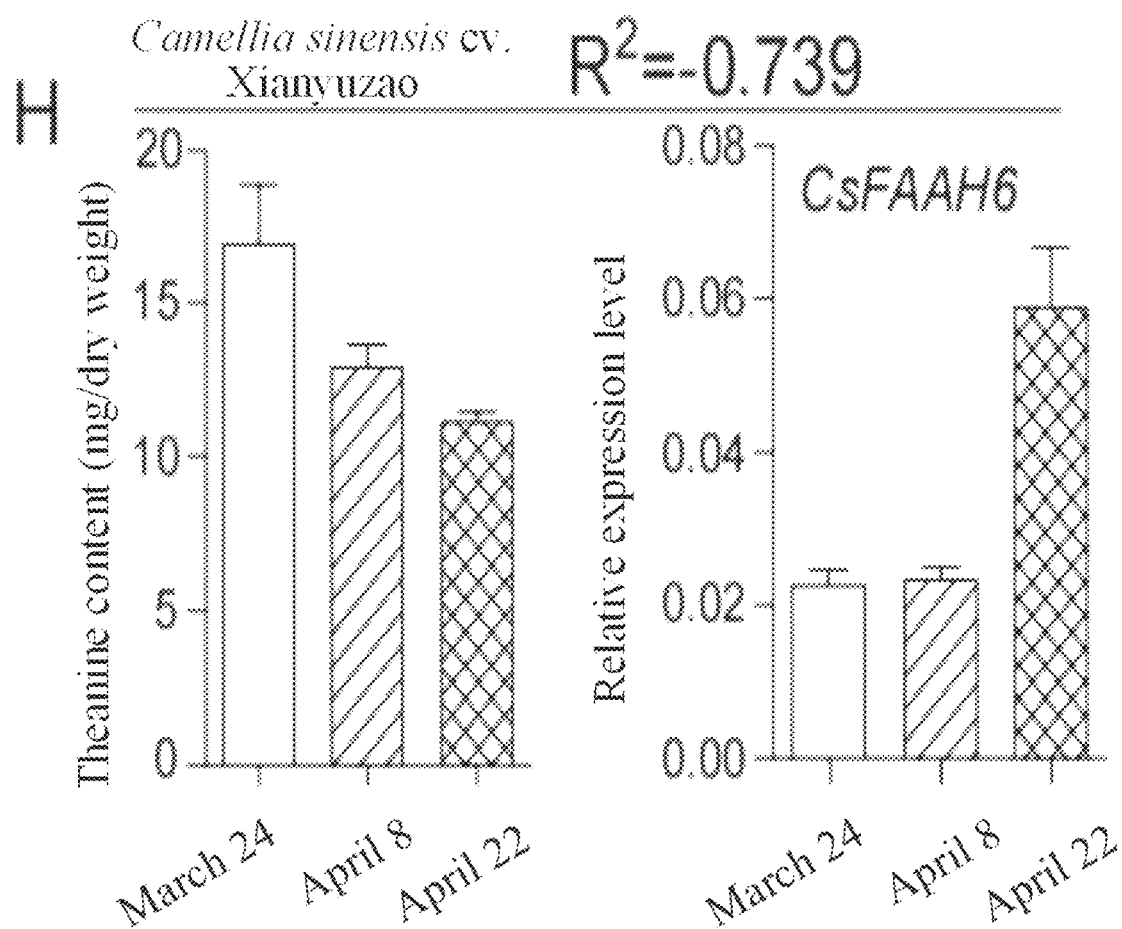
FIG. 4H illustrates the correlation between expression levels of CsFAAH6 in *C. sinensis* cv. Xianyuzao and theanine content in tea shoots.
Figure 4I:
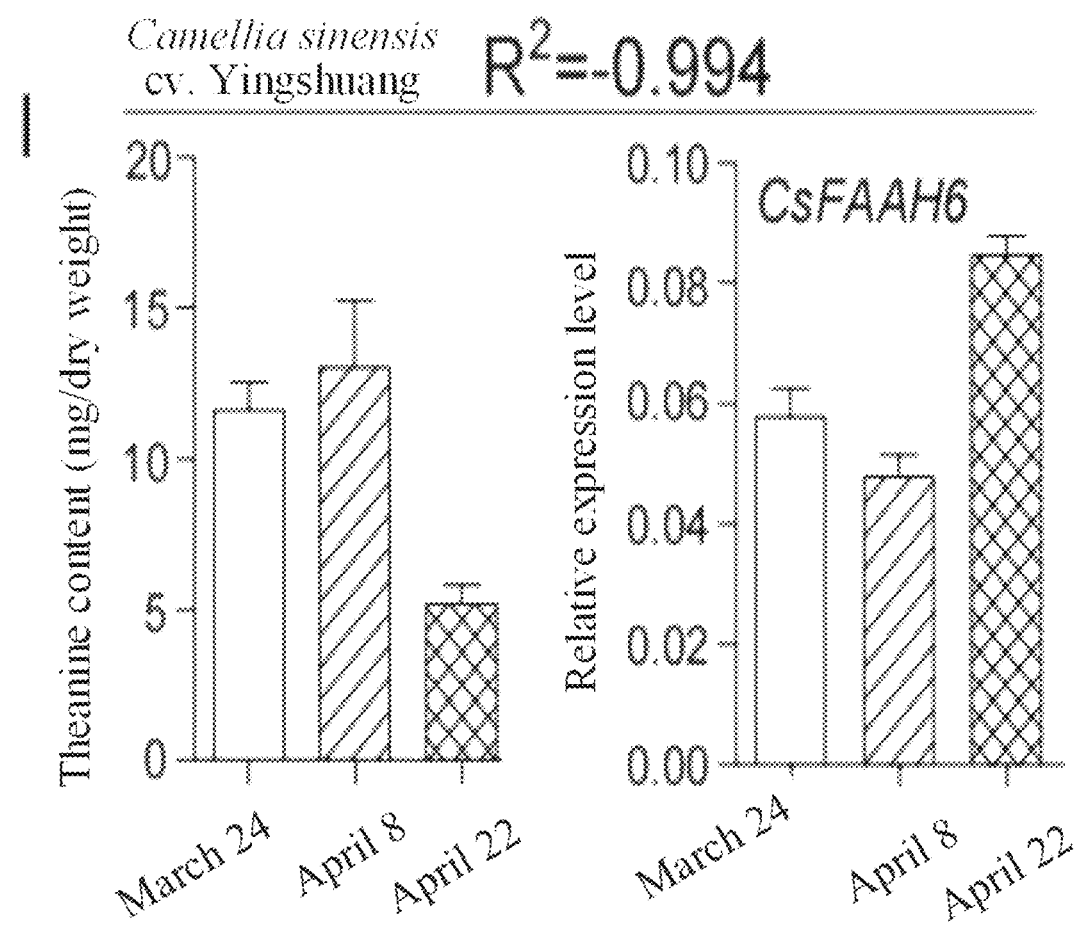
FIG. 4I illustrates the correlation between expression levels of CsFAAH6 in *C. sinensis* cv. Yingshuang and theanine content in tea shoots.

FIGS. 1A-B illustrates the expression of the CsFAAH6 gene in different tissues of tea plant. As can be seen from FIGS. 1A-B, the results of qRT-PCR showed that CsFAAH6 was expressed in various tissues, and the expression level in mature leaves was significantly higher than that in other parts.

3. Subcellular Localization of CsFAAH6 in Tea Plant Protoplasts (1) Construction of pCAMBIA1305.1-CsFAAH6 Vector Using pEASY-Blunt::CsFAAH6 plasmid as a template, based on the upstream primer (5'-GGACTAGTATGGG-CATTTTCAAGGCC-3') (SEQ ID NO: 9) and the downstream primer (5'-CGGGATCCATCCITTGAGCAGAT-CATAGAA-3') (SEQ ID NO: 10), PCR amplification was conducted. PCR products were recovered with 1.2% agarose gel electrophoresis bands. First, the recovered gene PCR product and the vector plasmid were double digested, and the digested product was recovered with a 1.2% agarose gel electrophoresis band. Using T4 DNA Ligase ligation technology, the band was digested with 2 μL of the vector and 6 μL of the gene, and the product was recovered. 1 μL of T4 DNA Ligase Mix and 1 μL of T4 DNA Ligase Buffer were left to stand overnight at 4° C., transformed into *E. coli* DH5. Competent Cells, and sent to Sangon for sequencing.

(2) Preparation of Tea Plant Protoplasts
  i) The petals of well-grown *C. sinensis* cv. Shuchazao plants were collected.
  ii) Using a sharp razor blade, the petals were cut into about 1 mm and put in a Petri dish (90×1.5 mm) containing 20 mL of enzymatic hydrolyzate.
  iii) The Petri dish was placed in a shaker at 20-25° C. (40 r/min) for 30-90 min to allow the protoplast cells to be fully enzymatically hydrolyzed from the petals.
  iv) The enzymatic hydrolyzate containing protoplasts were transferred into a 50 mL centrifuge tube, and centrifuged at 100×g for 3 min to collect protoplasts. The protoplasts were washed twice with 10 mL of pre-cooled W5 solution. The operation should be gentle to avoid cell disruption. The protoplasts were resuspended with an appropriate volume of W5 solution and placed on ice for a minimum of 30 min. During this period, the protoplasts were counted using a hemocytometer and the protoplast concentration was measured (if the concentration is too high, it can be diluted 10 to 20 fold and then determined).

(3) Transformation of Protoplasts
  i) The protoplasts were centrifuged at 100×g for 1 min, the supernatant was discarded, the protoplasts were resuspended with freshly prepared MMg solution, and the concentration was adjusted to $3-5\times10^5$ cells/mL.
  ii) 20 μL of pCAMBIA1305.1-CsFAAH6 plasmids were added to the bottom of a 5 mL centrifuge tube (if multiple plasmids are used for co-transformation, the transformed plasmids need to be premixed), 200 μL of MMg solution (containing $6-10\times10^4$ protoplast cells), and the bottom of the centrifuge tube was flicked to mix the mixture thoroughly.
  iii) 220 μL of the freshly prepared PEG4000 solution was added, and the centrifuge tube was slowly inverted to mix well and left to stand at room temperature for 5-30 min.

iv) The protoplasts were collected by centrifugation at 100×g for 1 min, and rinsed twice with 2 mL of W5 solution.

v) The protoplasts were resuspended with 0.6 mL of W5 solution and transferred to a 24-well plate for culture (the plate wells were soaked with 0.5-0.8 mL of 1% BSA for at least 30 min, and the BSA solution was discarded for use). After culturing at 20-23° C. for 14-18 h, the fluorescence signal was detected under a laser scanning confocal microscope.

As shown in FIGS. 2A-F, the CsFAAH6-fused green fluorescent protein (GFP) signal was specifically expressed in mitochondria of tea plant protoplast cells, while the empty vector GFP signal filled the whole tea plant protoplast cells.

4. Inhibition of CsFAAH6 Gene Expression can Significantly Increase the Theanine Content in Tea Leaves To verify whether CsFAAH6 has the function of degrading theanine in tea plants, antisense oligonucleotides were used to transiently silence CsFAAH6 in leaves. First, 250 μL of ddH$_2$O was added to four tubes each of sense (sODN) and antisense (AsODN) oligonucleotide primers of CsFAAH6 and mixed into one tube. The final concentration of the primers was 40 μM, and 330 μL was added to a 1.5 mL centrifuge tube for five replicates. The first, second, and third leaves of the tea shoot that had been dark-treated in advance were obliquely cut to an appropriate height and inserted into centrifuge tubes with primers, and the tubes were sealed with parafilm. The processed samples were inserted on the plate and put in a foam box with a small amount of water, sealed with plastic wrap, and placed in a phytotron for 24 h for sampling. RNA was extracted for fluorescence quantitative PCR analysis of gene expression, and the rest of the samples were freeze-dried. The theanine was extracted and the theanine content was detected by high performance liquid chromatography (HPLC).

As shown in FIGS. 3A-D, the leaves of the four biological replicates had different degrees of CsFAAH6 gene silencing; the detection results of theanine content in the leaves showed that the theanine content in the leaves of the four biological replicates significantly increased in the treatment group compared with the control (sODN). Combined with the high expression of CsFAAH6 in mature leaves and the mitochondrial subcellular localization of CsFAAH6, these results indicated that CsFAAH6 was involved in the cytological process of theanine degradation in tea shoots.

5. The Expression Level of CsFAAH6 in Tea Plant is Significantly Negatively Correlated with the Theanine Content in Tea Shoots The theanine content and the expression levels of CsFAAH6 in shoots (one bud and two leaves) of nine tea cultivars during three different periods in spring (on March 24, April 8, and April 22) were detected. As shown in FIGS. 4A-I, one-bud-two-leaf tea plant samples of the nine different cultivars during three periods (on March 24, April 8, and Apr. 22, 2020) were ground. RNA was extracted from the samples of the nine tea cultivars for fluorescence quantitative PCR analysis of CsFAAH6 gene expression; the theanine content in shoots of the nine different tea cultivars was detected by HPLC, and the correlation between gene expression level and theanine content of different cultivars during different periods was analyzed.

As shown in FIGS. 4A-I, the theanine content decreased significantly with the increase of the expression level of CsFAAH6, showing a significant negative correlation trend. Except for *C. sinensis* cv. Xianyuzao, the correlation coefficients of eight cultivars all exceeded −0.9. The correlation between the theanine content in shoots of different tea cultivars and CsFAAH6 further verified that CsFAAH6 has the function of theanine degradation.

The above content is only an example and description of the structure of the present disclosure. Those skilled in the art can make various modifications or supplements to the specific example described or replace them in a similar manner, as long as they do not depart from the structure of the present disclosure or go beyond the scope defined by the claims, all of which fall within the protection scope of the present disclosure.

---

What is claimed is:

1. A method for using a tea plant *Camellia sinensis* fatty acid amide hydrolase 6 (CsFAAH6) gene to lower theanine content in tea shoots and roots, comprising the following steps:
cloning a tea plant CsFAAH6 gene sequence encoding the protein of SEQ ID NO:2;
constructing a tea plant expression vector comprising the CsFAAH6 gene sequence; and
transforming the tea plant expression vector into the tea shoots and roots, thereby expressing the gene sequence and lowering the theanine content in tea shoots and roots.

2. The method according to claim 1, wherein the tea plant CsFAAH6 gene sequence comprises SEQ ID NO: 1.

* * * * *

SEQUENCE LISTING

```
Sequence total quantity: 10
SEQ ID NO: 1            moltype = DNA   length = 1824
FEATURE                 Location/Qualifiers
source                  1..1824
                        mol_type = other DNA
                        note = Tea tree (Camellia sinensis (L.) O. Kuntze)
                        organism = synthetic construct
SEQUENCE: 1
atgggcattt tcaaggccaa aggcgtagtc tacaagcctg tcgacgatgt cgatctcggt    60
cctcacagcg atgagttta tctccgtgct aacgtcaaag ctcctcgcat ggctggattg   120
ctggttaaaa tttttgtttg gttcctcgag tcgcggattt tcgggggtat tttgttgtac   180
atgttgaaga gaaacaacct aattcacaag cttgtttcat atgcagagtt ggaagagtca   240
cctgtatttg ttccttcaca cccttatgaa ggccttaaag aacaagaagt caaattagta   300
gaggatgatc tctctccatc tgacaaaatt cagaaggcca tggaatgcat acaatgctca   360
gaaagtatac aagaaaattc ggagcttagt ttccatcgct ggacagtatt ggattattca   420
agagcttaca tttcaggaga gattactcct ctcatggtgg cggagcgatt tatagctgct   480
gtccatgaat cgtctgaacc tgcattgcac atgtcattct ttattgatta taatgttgga   540
gacatattaa ggcaagctac tgagtcaact cagcggtaca aacaaggaga accattatca   600
cctctagatg gagtcccaat cgcaatcaaa gacgaaatag attgtatgcc ctatccaact   660
acagggggta caaagtggtt gcaaaaggta agacattgtg cagatgatgc atgctgtgtt   720
aagcgcctga gattatgtgg tgccatactt gttgggaaga caaatatgca tgagctcggg   780
gctggaacca gtggtatcaa tcctcattat ggggtaccta gaaatccata tgatcccaac   840
aaggtctctg ggggttcttc tagtggatct gcagctgtgg tttctgcagg gttgtgccct   900
gttgccctga gtgttgatgg gggaggaatc gtgagaatgc ctgctgctct ttgtggtgtt   960
gttggtctga agccaacttt tggacgtgtg ccccattctg gtgttattcc tctgaactga  1020
acagttggga tggtcggtat cctagcaggc acagttgaag atgcatttat tacttatgca  1080
gctatcagtg gtcaatttcc atcatgccaa cccacagatg cagtgaaaaa aattaatttc  1140
ccactcctga agacaccaaa ctgtatatct aacatcaaga tggctaaata tggggagtgg  1200
tttaatgatt gcaccgacga catcagagtc tgttgttccc atgctctgga ccagcttcac  1260
```

```
aagcattatg gatgggagac catggacgtg accataccag agatagaggt gatgcgcctg   1320
gcgcattatt caacaattgg atcggagtgt agcaattcaa ttgcttgtca tcttgaaaac   1380
atgaatgtgg cagaaatagg gttggatgca agagtagcac tctctgttta tggttctttc   1440
agcagcaggg agtatttgaa tgcccagaaa attaggaacc gacagatgca gtttcataag   1500
aaaatatttg ccatggcaga tgttattgtt acaccaacag caggtgtgac tgcctaccca   1560
atattcgatg atgctttgaa aactggggaa cttgactaca taaatggagc tgcacttgtt   1620
cggtatcaga tatcaggaaa tttcttggga ttgccagcag taaccatacc tattggatac   1680
gacaaagttg gcttgcctat aggccttcaa tttattggga agccatggtc cgaagctacg   1740
ctgatccaca tagcgttcgc aatgcaggcc atctcggact caaaaaaacc acagattttc   1800
tatgatctgc tcaaaaagga ttga                                          1824

SEQ ID NO: 2               moltype = AA   length = 607
FEATURE                    Location/Qualifiers
source                     1..607
                           mol_type = protein
                           note = Tea tree (Camellia sinensis (L.) O. Kuntze)
                           organism = synthetic construct
SEQUENCE: 2
MGIFKAKGVV YKPVDDVDLG PHSDEFYLRA NVKAPRMAGL LVKIFVWFLE SRIFGGILLY    60
MLKRNNLIHK LVSYAELEES PVFVPSHPYE GLKEQEVKLV EDDLSPSDKI QKAMECIQCS   120
ESIQENSELS FHRWTVLDYS RAYISGEITP LMVAERFIAA VHESSEPALH MSFFIDYNVG   180
DILRQATEST QRYKQGEPLS PLDGVPIAIK DEIDCMPYPT TGGTKWLQKV RHCADDACCV   240
KRLRLCGAIL VGKTNMHELG AGTSGINPHY GVPRNPYDPN KVSGGSSSGS AAVVSAGLCP   300
VALGVDGGGS VRMPAALCGV VGLKPTFGRV PHSGVIPLNW TVGMVGILAG TVEDAFITYA   360
AISGQFPSCQ PTDAVKKINF PLLKTPNCIS NIKMAKYGEW FNDCTDDIRV CCSHALDQLH   420
KHYGWETMDV TIPEIEVMRL AHYSTIGSEC SNSIACHLEN MNVAEIGLDA RVALSVYGSF   480
SSREYLNAQK IRNRQMQFHK KIFAMADVIV TPTTGVTAYP IFDDALKTGE LDYINGAALV   540
RYQISGNFLG LPAVTIPIGY DKVGLPIGLQ FIGKPWSEAT LIHIAFAMQA ISDSKKPQIF   600
YDLLKKD                                                             607

SEQ ID NO: 3               moltype = DNA   length = 20
FEATURE                    Location/Qualifiers
source                     1..20
                           PCR_primers =
                           fwd_name:CsFAAH6_F,fwd_seq:atgggcattttcaaggccaa,rev_name:Cs
                           FAAH6_R,rev_seq:tcaatccttttgagcagatca
                           mol_type = other DNA
                           note = upstream primer for CsFAAH6 gene
                           organism = synthetic construct
SEQUENCE: 3
atgggcattt tcaaggccaa                                                20

SEQ ID NO: 4               moltype = DNA   length = 22
FEATURE                    Location/Qualifiers
source                     1..22
                           PCR_primers =
                           fwd_name:CsFAAH6_F,fwd_seq:atgggcattttcaaggccaa,rev_name:Cs
                           FAAH6_R,rev_seq:tcaatccttttgagcagatca
                           mol_type = other DNA
                           note = downstream primer for CsFAAH6 gene
                           organism = synthetic construct
SEQUENCE: 4
tcaatccttt ttgagcagat ca                                             22

SEQ ID NO: 5               moltype = DNA   length = 20
FEATURE                    Location/Qualifiers
source                     1..20
                           PCR_primers =
                           fwd_name:CsFAAH6_F,fwd_seq:gttctttcagcagcagggag,rev_name:Cs
                           FAAH6_R,rev_seq:cgaacaagtgcagctccatt
                           mol_type = other DNA
                           note = upstream primer for CsFAAH6 gene
                           organism = synthetic construct
SEQUENCE: 5
gttctttcag cagcagggag                                                20

SEQ ID NO: 6               moltype = DNA   length = 20
FEATURE                    Location/Qualifiers
source                     1..20
                           PCR_primers =
                           fwd_name:CsFAAH6_F,fwd_seq:gttctttcagcagcagggag,rev_name:Cs
                           FAAH6_R,rev_seq:cgaacaagtgcagctccatt
                           mol_type = other DNA
                           note = downstream primer for CsFAAH6 gene
                           organism = synthetic construct
SEQUENCE: 6
cgaacaagtg cagctccatt                                                20

SEQ ID NO: 7               moltype = DNA   length = 19
```

-continued

```
FEATURE                 Location/Qualifiers
source                  1..19
                        PCR_primers =
                         fwd_name:CsFAAH6_F,fwd_seq:ttggcatcgttgagggtct,rev_name:CsF
                         AAH6_R,rev_seq:cagtgggaacacggaaagc
                        mol_type = other DNA
                        note = upstream primer for CsFAAH6 gene
                        organism = synthetic construct
SEQUENCE: 7
ttggcatcgt tgagggtct                                                  19

SEQ ID NO: 8            moltype = DNA  length = 19
FEATURE                 Location/Qualifiers
source                  1..19
                        PCR_primers =
                         fwd_name:CsFAAH6_F,fwd_seq:ttggcatcgttgagggtct,rev_name:CsF
                         AAH6_R,rev_seq:cagtgggaacacggaaagc
                        mol_type = other DNA
                        note = downstream primer for CsFAAH6 gene
                        organism = synthetic construct
SEQUENCE: 8
cagtgggaac acggaaagc                                                  19

SEQ ID NO: 9            moltype = DNA  length = 26
FEATURE                 Location/Qualifiers
source                  1..26
                        PCR_primers =
                         fwd_name:pCAMBIA13051_F,fwd_seq:ggactagtatgggcatttcaaggcc,
                         rev_name:pCAMBIA13051_R,rev_seq:cgggatccatcctttttgagcagatc
                         atagaa
                        mol_type = other DNA
                        note = upstream primer for constructing
                         pCAMBIA1305.1-CsFAAH6 vector
                        organism = synthetic construct
SEQUENCE: 9
ggactagtat gggcattttc aaggcc                                          26

SEQ ID NO: 10           moltype = DNA  length = 33
FEATURE                 Location/Qualifiers
source                  1..33
                        PCR_primers =
                         fwd_name:pCAMBIA13051_F,fwd_seq:ggactagtatgggcatttcaaggcc,
                         rev_name:pCAMBIA13051_R,rev_seq:cgggatccatcctttttgagcagatc
                         atagaa
                        mol_type = other DNA
                        note = downstream primer for constructing
                         pCAMBIA1305.1-CsFAAH6 vector
                        organism = synthetic construct
SEQUENCE: 10
cgggatccat cctttttga gcagatcata gaa                                   33
```